United States Patent [19]
Miller

[11] Patent Number: 5,796,340
[45] Date of Patent: Aug. 18, 1998

[54] MOTION MONITOR USEFUL FOR SLEEPING HUMANS

[76] Inventor: William Miller, 1735 Caminito Ardiente, La Jolla, Calif. 92037

[21] Appl. No.: 698,038

[22] Filed: Aug. 12, 1996

[51] Int. Cl.$^6$ ..................................................... G08B 23/00
[52] U.S. Cl. ........................... 340/573; 128/671; 128/721; 128/782
[58] Field of Search ..................................... 340/573, 666, 340/665, 529; 128/721, 722, 782, 670, 671; 5/655, 655.3, 706, 707, 709

[56] References Cited

U.S. PATENT DOCUMENTS

| | | | |
|---|---|---|---|
| 3,727,606 | 4/1973 | Sielaff | 128/722 |
| 3,926,177 | 12/1975 | Hardway et al. | 128/722 |
| 4,033,332 | 7/1977 | Hardway et al. | 128/722 |
| 4,146,885 | 3/1979 | Lawson | 128/721 |
| 4,359,726 | 11/1982 | Lewiner et al. | 340/573 X |
| 4,509,527 | 4/1985 | Fraden | 128/671 |
| 4,732,159 | 3/1988 | Kraman | 128/721 |
| 5,197,490 | 3/1993 | Steiner et al. | 128/782 |

OTHER PUBLICATIONS

Videotape copy of a segment entitled "Bio-Mat", which aired on the Discovery Channel program entitled Beyond 2000 on Oct. 21, 1996. Applicant has been advised by Discovery Channel that the Bio-Mat segment aired as early as Apr. 1996.

*Primary Examiner*—Thomas Mullen
*Attorney, Agent, or Firm*—Fliesler Dubb Meyer & Lovejoy LLP

[57] ABSTRACT

A motion monitor which detects respiration and/or cardiac activity of a human, particularly a sleeping human, has a mattress, for example, an air mattress, for supporting a sleeping human. The mattress has an interior cavity isolated from and at a pressure equal to or greater than ambient atmospheric pressure. A pressure transducer is connected with the interior cavity of the mattress and generates a signal representative of the pressure in the interior cavity. An indication unit is connected to the pressure transducer and presents a signal based on the output of the pressure transducer. This sleep monitor is useful for infants, particularly infants at risk for sudden infant death syndrome (SIDS).

4 Claims, 3 Drawing Sheets

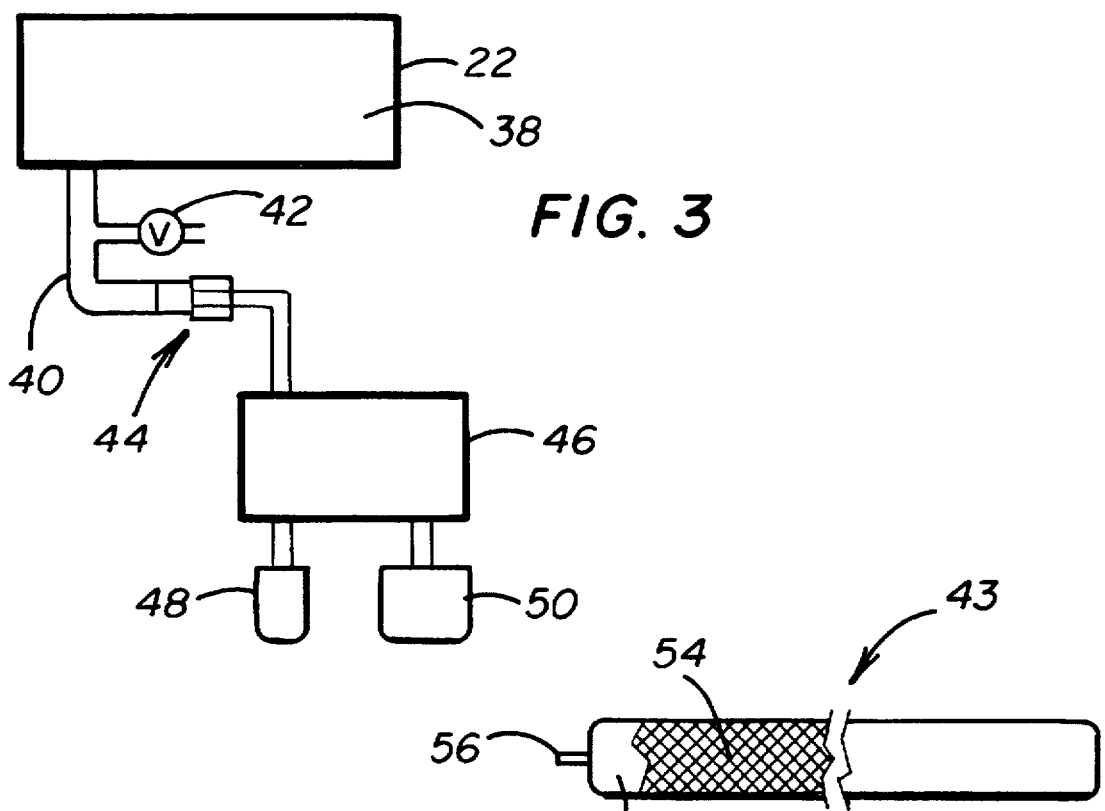
FIG. 3
FIG. 4
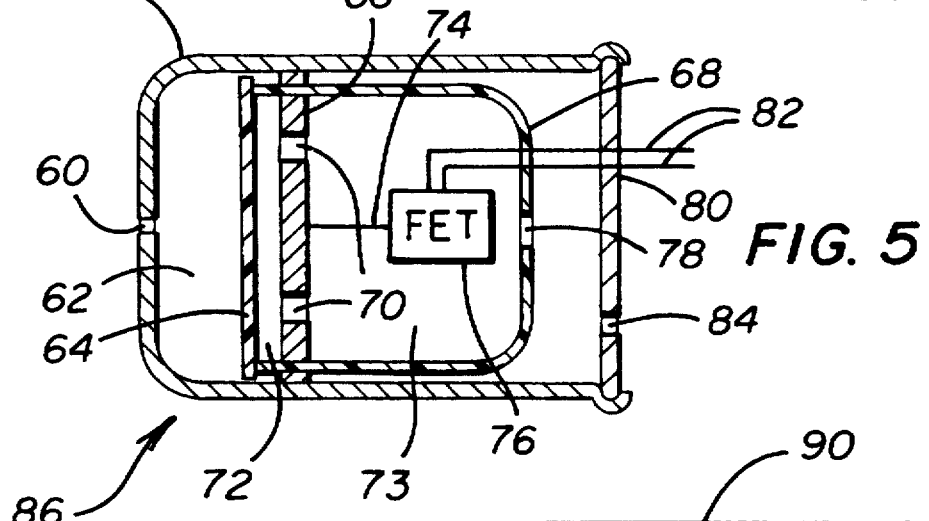
FIG. 5
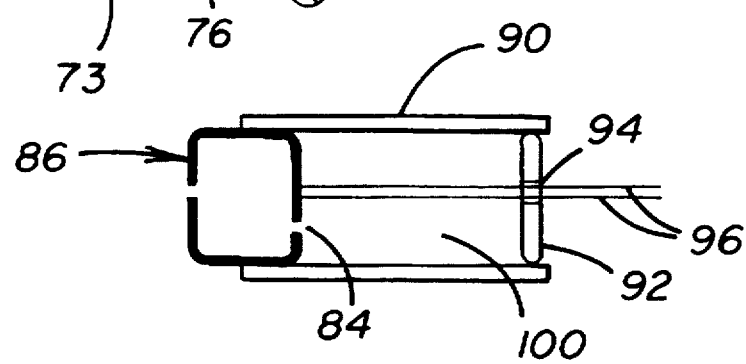
FIG. 6

1

MOTION MONITOR USEFUL FOR SLEEPING HUMANS

BACKGROUND OF THE INVENTION

1. Field of the Invention

The present invention relates to motion monitors, particularly sleep monitors useful with children suspected of being at risk for sudden infant death syndrome ("SIDS").

2. Description of the Related Art

Sleep monitors are used to detect occurrences of apnea (transient cessation of respiration), bradycardia (relatively slow heart action), and tachycardia (relatively rapid heart action) when there is some medical reason to believe that infants (or adults) are at risk for these events. A sleep monitor can also be used with infants who are suspected of being at risk for SIDS. SIDS, which affects one out of every 500 to 600 live births, is the largest single cause of death among infants less than one year of age, and accounts for 6,000 to 10,000 deaths per year in the United States.

Conventional sleep monitors measure respiration and heart action by measuring transthoracic impedance and the electrocardiogram (TTI/ECG) and are designed to sound an alarm when apnea, bradycardia or tachycardia is detected and found to persist for more than a predetermined amount of time. The measurements taken by conventional sleep monitors are electrical in nature, and require attaching electrodes to the subject's skin, usually on the chest. Wires from a control box are attached to the electrodes, and a band is wrapped around the chest to keep the wires in place during sleep. The electrodes must be attached each time the subject goes to sleep, and the band, the electrodes and the wires must be removed at the end of each sleep session. Special care must be taken to assure good electrical contact between the electrodes and the skin. Foreign matter on the skin, such as talc, can cause a faulty contact. Motion of the subject during sleep can cause electrical noise at the contacts, can cause the wires to come loose, or can cause the wires to break. In a recent study in which 182 patients were monitored in their sleep, of 30,059 recorded events (i.e., machine-indicated occurrences of apnea and/or bradycardia and/or tachycardia) 91.9% were false alarms. 68.5% of the recorded events were false alarms caused by body motion and/or loose leads, and 23.4% were other machine errors such as interpretation of a low-amplitude respiratory signal as apnea. In addition to the functional problems of using a sleep monitor, there is also the matter of cost. The rental fee for such a machine is several hundred dollars per month. Weese-Mayer DE, Morrow AS, Conway LP et al., *Assessing clinical significance of apnea exceeding 15 seconds with event recording.* J. Pediatrics 117:568, 1990. Also see Nathanson I, O'Donnell J, Commins MF Am Dis Child 143:476.

SUMMARY OF THE INVENTION

The invention described herein is a motion monitor which is simpler to use, more reliable, and lower in cost than what is now available. In particular, the monitor of the present invention operates without attaching leads to the human being monitored and no wires are brought into the crib or bed. In accordance with the present invention, a subject to be monitored sleeps on a mattress having an interior region (or cavity) isolated from ambient atmospheric pressure. Motion of the subject, including breathing and heartbeats, cause a change in pressure in the interior region of the mattress. A pressure transducer measures the change in pressure and generates a signal representative of a pressure change. A visual or audible signal indicates activity and/or a lack of activity and an alarm can be generated if a lack of activity persists for greater than a predetermined time period.

A monitor in accordance with the present invention includes a mattress for supporting a human, the mattress having an interior cavity isolated from and at a pressure equal to or greater than ambient atmospheric pressure, a pressure transducer in communication with the interior cavity which generates a signal representative of the pressure in the interior cavity, and an indication unit connected to the pressure transducer which presents visual and/or audible signals based on the signal generated by the pressure transducer.

BRIEF DESCRIPTION OF THE DRAWINGS

FIG. 3 is a schematic illustration of a monitor in accordance with the present invention including a mattress, a transducer, and an indication unit;

FIG. 4 is a sectional view of a self-inflating mattress for use in the monitor of the present invention;

FIG. 5 is a sectional view of an electret condenser microphone useful as a transducer in the monitor of the present invention;

FIG. 6 is sectional view of an electret condenser microphone having improved low frequency response and a housing for the microphone.

DESCRIPTION OF THE PREFERRED EMBODIMENTS

A motion monitor as described below includes a pressure sensor, for example a mattress, on which a human rests or sleeps. A mattress to be used as a pressure sensor has a sealed interior region maintained at or above atmospheric pressure. Cardiac and respiratory actions of the human produce characteristic pressure variations in the interior region of the mattress. A transducer converts these pressure variations into electrical signals. A controller analyzes the electrical signals output by the transducer and generates status indications and alarms.

The Sensor. Cardiac and respiratory processes of either sleeping, comatose or waking humans cause various parts of the body to move and thereby undergo transient accelerations (changes in velocity). It is a fundamental principle of physics (Newton's second law of motion) that for any small particle of mass (m) to undergo an acceleration (a) there must be a net force (ma) acting on the mass. This is normally stated in the form of the equation F=ma. For a complex mass, such as a human body, in which different parts of the body are undergoing different accelerations, this law is still true, with the understanding that (m) is the mass of the entire body, and (a) is the acceleration of the center of gravity of the body.

Figure 1:
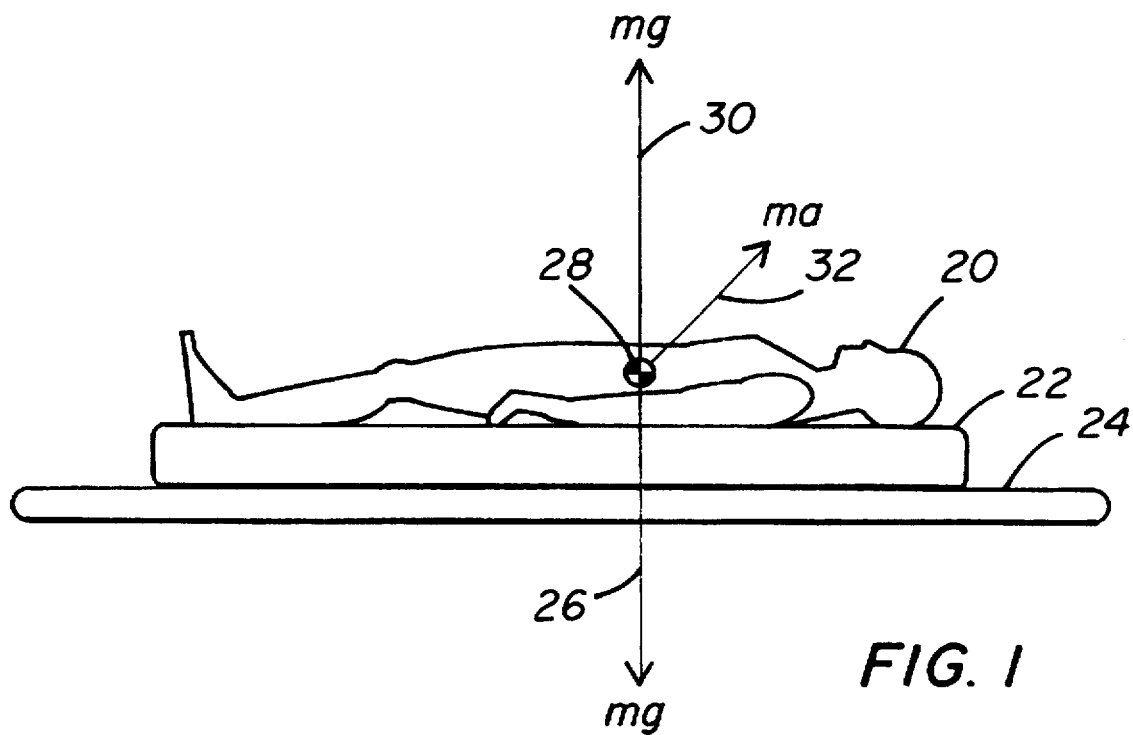
FIG. 1 is a schematic illustration of a human on a mattress.

In FIG. 1 a human 20—either an infant, toddler, adolescent, or adult—of total mass m is lying on a mattress 22 which is supported on a rigid, unmoving surface 24. The earth exerts a downward gravitational force on each small mass of the human 20, and the sum of all these forces is a single force mg 26 acting through the center of gravity 28 of the human 20. If the human 20 is motionless, then the net force on the body is zero. Thus, there is an additional force mg 30, equal and opposite to mg 26, acting on the human 20. This upward force mg 30 is provided by the mattress 22.

If the human 20 is not motionless, and its center of gravity 28 is undergoing a varying acceleration (a) then the net force on the human 20 is ma 32 rather than zero. The downward gravitational force mg 26 on the human is constant, so, for the net force on the body to be equal to ma 32, the force exerted by the mattress 22 must have two parts, the constant upward force mg 30 and a varying part ma 32.

Figure 2:
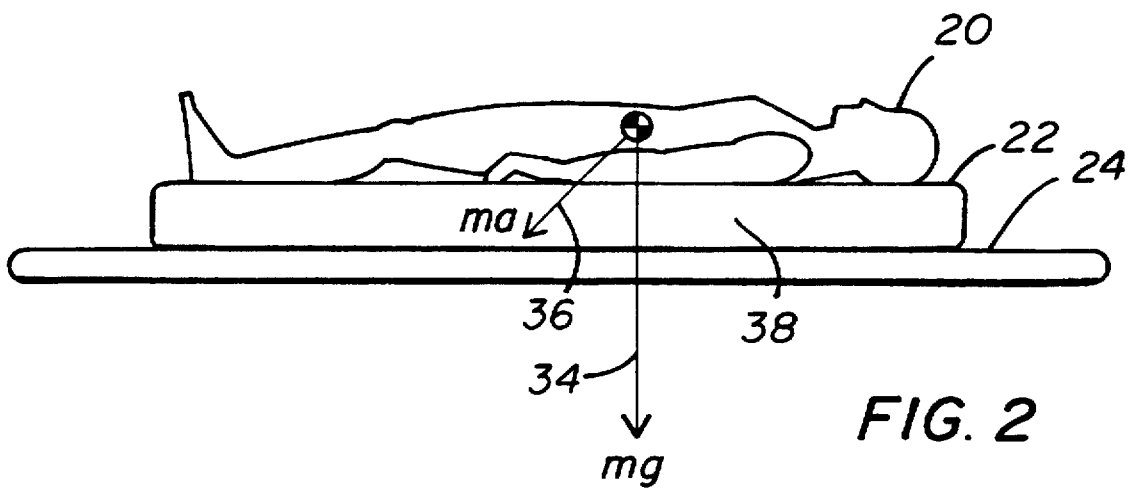
FIG. 2 is another schematic illustration of a human on a mattress.

It is a another basic principle of physics that for every action there is an equal and opposite reaction. The three forces shown in FIG. 1 all act upon the resting or sleeping human. The downward force mg 26 is exerted on the body by the earth, and the reaction to this force is an upward force of mg exerted on the earth which is not shown here. The two other forces, mg 30 and ma 32, are exerted on the human 20 by the mattress 22, and the reactions to these forces, shown in FIG. 2, are a downward force mg 34 and a force ma 36, both exerted on the mattress 22. If the surface of the mattress 22 is airtight, and the interior region of the mattress is filled with air, then the air pressure within the mattress would vary as the force ma 36 varies. Thus, the changes in pressure in the interior region 38 of mattress 22 will give some indication of respiratory and cardiac action, without attachment of any apparatus to the human 20 being monitored. This analysis of the forces on a resting or sleeping human applies to pressure sensors other than mattresses such as sensors placed under or incorporated in the legs or a bed or crib.

In its simplest form, the mattress 22 is an airtight rectangular parallepiped having an interior region 38 filled with air. It is useful to pressurize this air in interior region 38 to slightly greater than ambient atmospheric pressure so that the mattress will hold its shape, and also so that the top and bottom of the mattress will not touch when a human 20 lies on the mattress 22. A standard inflatable air mattress used for camping is one example of mattress 22.

FIG. 3 shows a flexible tube 40 sealed to the mattress 22 and connected to the interior 38 of the mattress 22. One end of the tube 40 is connected to a transducer 44. A valve 42 may be connected to flexible tube 40 and used to pressurize the mattress 22. Before the mattress 22 is used, valve 42 is opened, a pump (not shown) is attached to valve 42 and used to pressurize the mattress (or the mattress can be inflated by blowing into valve 42), and the valve 42 is then closed. This process of pressurizing the mattress can be avoided if a self-inflating mattress is used.

Another example of mattress 22 is a self-inflating mattress 43, shown in FIG. 4. The self-inflating mattress 43 is made by filling a mattress shell 52 with open-celled foam 54 which is bonded to the interior of the mattress shell 52. The foam 54 should have a relatively low stiffness and there should be just enough foam to cause the mattress 43 to expand to its full size when there is no load on the mattress. To use the system, the valve 42 is opened for a few moments, until the mattress expands to full size. The valve 42 is then closed and the mattress 43 is ready for use. If the self-inflating mattress 43 is made with its own valve 56, then valve 56 is opened to expand the mattress and then closed. One example of a self-inflating mattress 43 is the Therm A Rest made by Cascade Designs, Inc.

The mattress used in the present monitor system may be placed on top of or below a standard mattress. Alternatively, the mattress may be used in place of a standard mattress.

The Transducer. One purpose of the present monitor system is to produce a visual or audible indication of the status of respiration and cardiac action. To provide such an indication it is useful to convert the pressure variations in interior region 38 of mattress 22 into electrical signals. The pressure variations consist of (1) a time-independent part corresponding to the force of magnitude mg, (2) a time dependent part corresponding to respiration (usually twenty to thirty repetitions per minute), and (3) a time-dependent part corresponding to cardiac action (usually in the range of eighty to ninety repetitions per minute). The sum of the time-dependent respiration part (2) and the time-dependent cardiac part (3) corresponds to the force ma 32.

One sensitive, low-noise, reliable, and low-cost pressure transducer is an electret condenser microphone (ECM) 86 shown in FIG. 5. ECMs designed for use in the audio range, i.e, 20 to 20,000 Hz, are commercially available. In order for an ECM to detect the pressure variations within interior region 38, the response range of the ECM must be extended to frequencies below 20 Hz. In general, the response of an ECM at frequencies below 20 Hz is limited by air leakage, as discussed below.

ECM 86 has a cylindrical aluminum shell 58 having an input opening 60 which permits pressure variations to reach an air space 62 in front of a flexible condenser plate 64. The aluminum shell 58 is crimped around a circular flat circuit board 80. The air space 72, between the movable plate 64 and the fixed plate 66, is connected, via two holes 70 in the fixed plate, to the air space 73 behind the fixed plate in order to prevent the motion of the flexible plate from producing a large pressure variation in the region 72. The combined region 72 and 73 is bounded by a rigid plastic shell 68 and the flexible capacitor plate 64. Shell 68 has a small hole at 78. As the permanently polarized flexible plate (the electret) 64 responds to the pressure changes in the space 62 and causes the distance between the two condenser plates to vary, the voltage between the plates will vary. The voltage between the plates is applied to the input terminal 74 of the field effect transistor (FET) 76. The output leads of the FET 76 are shown at 82. There is some leakage between the air space 62 and the combined spaces 72 and 73. If the pressure in the region 62 rises by some fixed amount and is maintained at this elevated value, then the plate 64 will initially move toward plate 66. However, as air leaks from region 62 to the regions 72 and 73 the pressure in region 72 will reach the same value as that in region 62, plate 64 will return to its original position and the voltage output to the FET will return to zero. The time required for the pressures in regions 62 and 72 to equalize depends on the leakage rate and the volume of the regions 72 and 73. For example, if a steady pressure increment is applied in region 62 and the pressure in region 72 rises to this value in about 1/10 of a second, then the response of the ECM will fall off for frequencies below 10 Hz.

The response of the ECM 86 can be extended to lower frequencies by slowing the rate at which the pressure equalizes in regions 62 and 72. This can be done either by slowing the leakage rate or by adding to the volume in regions 72 and 73. The latter method can be accomplished by an external modification to the microphone. In FIG. 6, the microphone 86 has a cylinder 90 fitted snugly over the microphone 86. A plate 92 seals the far end of the cylinder 90. The wires 96 from the field effect transistor exit through a small hole 94 in plate 92. An airtight sealant is applied in the hole 94 around the wires 96. A small hole 84 has been bored through the circuit board 80 (FIG. 5) to connect regions 72 and 73 in the microphone with region 100 (FIG. 6), thereby increasing the time required for the leakage to cause equalization of the pressures in regions 62 and 72.

An example of a combined sensor and transducer useful in the monitor of the present invention is an electronic pressure sensor of the type used in digital scales. Sensors of this type provide an electrical signal representative of the pressure exerted on the sensor. An electronic sensor of this type could be placed under one or more legs of a crib or bed or incorporated into one or more legs of the crib or bed.

The Controller. A controller 46, as shown in FIG. 3, includes a D.C. power supply for the microphone 86, data acquisition and analysis circuitry, a display and/or an alarm. Examples of a display includes bar type displays or other displays which provide an indication that the human on mattress 22 is breathing and/or has a heart rate either in real time or by an indicator which stays lit as long as signals are received from transducer 44 within a predetermined time. Likewise an audible alarm could be set to go off if signals corresponding to breathing and/or heart beats are not received within a predetermined time. Controller 46 could be attached to the side or end of the crib. Additional displays 48 and alarms 50 can be located remotely for example, in other parts of a home. The connection between the controller 46 and the remote units 48 and 50 can be hardwired or wireless. The electrical signals output by ECM 86 reach controller 46 via wires 45. If it is desired to digitize this signal an analog to digital converter (ADC) can be connected to the output of ECM 86. Although a variety of sophisticated signal processing techniques could be applied to the signal, for example, to determine the pulse and respiration rates, a much simpler procedure might be more suitable for home monitoring. One could use the incoming signal to drive an array of light emitting diodes arranged in a vertical line. If there were 10 light emitting diodes in the array, the input voltage range could be divided into 10 parts, each corresponding to one of the diodes. As the incoming signal varied, the light would come from different parts of the array. If the signal went off scale, the uppermost or the lowest diode would be lit. For a steady zero amplitude signal one led at the center of the array would stay lit, and when this occurred for more than a predetermined amount of time, for example 15 seconds, an alarm would sound. When the alarm does not sound, a parent need only glance at the display, which might be in the living room of the home, and get immediate confirmation that there is respiratory or cardiac motion.

Figure 7:
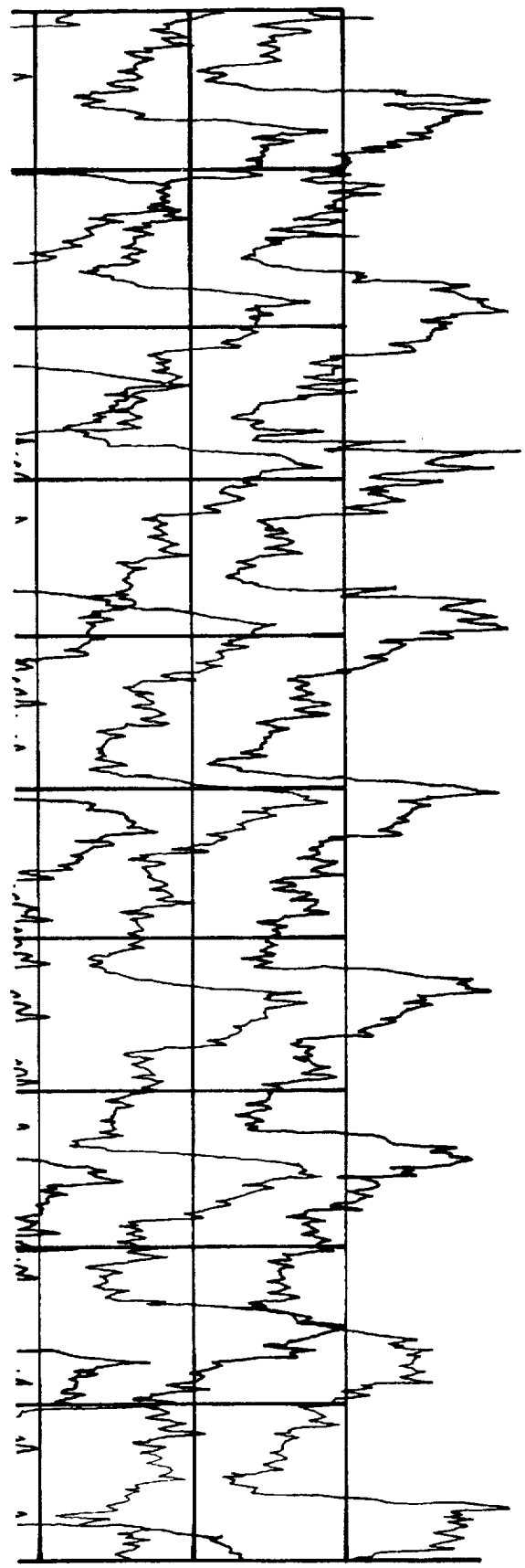
FIG. 7 is a graph showing signals generated by monitoring a sleeping human using the monitor of the present invention.

Experimental Results. FIG. 7 is a graph of the data obtained with a seven month old baby, and represents pressure (y axis) vs time (x axis) in a mattress 22. No amplification was applied to the signal output from transducer 44. The sampling rate was 100 samples per second and the input voltage range of the analog to digital converter was ±128 millivolts. The vertical lines on the graph are spaced at intervals of 2 seconds. The signal corresponding to respiration is a large, slow oscillation with a period of about 2.2 seconds and an amplitude of about 50 millivolts. The signal corresponding to cardiac action is a smaller amplitude, damped oscillation with a repetition rate of about 1.5 per second. The relative amplitudes of the respiratory and cardiac signals can change if the baby changes position. For example, when the baby turns itself or moves its limbs the signal amplitude can exceed the input range of the ADC.

What is claimed is:

1. A monitor, comprising:

a mattress for supporting a human, said mattress having an interior cavity isolated from and at a pressure equal to or greater than ambient atmospheric pressure;

an electret condenser microphone in communication with said interior cavity to generate a signal representative of the pressure in said interior cavity, said electret condenser microphone having a frequency response extending below 20 Hz and a substantially unaltered frequency response at and above 20 Hz; and an indication unit, electronically interconnected to said pressure transducer, which displays the signal generated by the pressure transducer.

2. A monitor according to claim 1, wherein said mattress is a self-inflating air mattress.

3. A monitor according to claim 1, wherein said electret condenser microphone includes:

a housing defining an interior region and having an input opening, said input opening being in communication with said interior cavity of said mattress;

a flexible condenser plate attached to said housing and dividing said interior region of said shell into an input region in communication with said input opening and a second region; and a cap connected to said housing to provide a third region in communication with and increasing the volume of said second region.

4. A monitor according to claim 1, wherein said indication unit includes an alarm which generates an audible alarm if changes in the signals representative of the pressure in the interior cavity do not exceed a predetermined value for a predetermined period.

* * * * *